United States Patent

Kühle et al.

[11] 3,931,317
[45] Jan. 6, 1976

[54] N-TRIFLUOROMETHYL-N-(TRIHALOMETHYLTHIO)-AMINO-BENZO-IMIDE CHLORIDES

[75] Inventors: Engelbert Kühle, Bergisch-Gladbach; Erich Klauke, Odenthal, both of Germany

[73] Assignee: Bayer Aktiengesellschaft, Leverkusen, Germany

[22] Filed: June 14, 1974

[21] Appl. No.: 479,385

[30] Foreign Application Priority Data
July 4, 1973  Germany............................ 2333939

[52] U.S. Cl.............................. 260/566 D; 424/325
[51] Int. Cl.²........................................ C07C 119/00
[58] Field of Search................................ 260/566 D

[56] References Cited
UNITED STATES PATENTS 3,714,182   1/1973   Bandurco et al. ............... 260/566 D
3,715,396   2/1973   Bandurco et al. ............... 260/566 D

*Primary Examiner*—Gerald A. Schwartz
*Attorney, Agent, or Firm*—Burgess, Dinklage & Sprung

[57] ABSTRACT

N-trifluoromethyl-N-(trihalomethylthio)-amino-benzo-imide chlorides of the formula

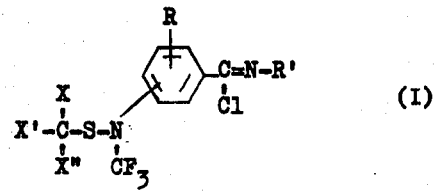

in which
X, X' and X'' each independently is fluorine, chlorine or bromine,
R is hydrogen, halogen, nitro, trifluoromethyl, or alkyl or alkoxy each with up to 3 carbon atoms, and
R' is alkyl with up to 16 carbon atoms, cycloalkyl with up to 7 carbon atoms, aralkyl with a total of up to 8 carbon atoms, or aryl with up to 10 carbon atoms, which possess fungicidal properties, and processes for their preparation from the corresponding benzoic acid amides by reaction with a chlorine-transfer agent.

5 Claims, No Drawings

N-TRIFLUOROMETHYL-N-(TRIHALOMETHYL-THIO)-AMINO-BENZO-IMIDE CHLORIDES

The present invention relates to and has for its objects the provision of particular new N-trifluoromethyl-N-(trihalomethylthio)-amino-benzo-imide chlorides, which possess fungicidal properties, active compositions in the form of mixtures of such compounds with solid and liquid dispersible carrier vehicles, and methods for producing such compounds and for using such compounds in a new way especially for combating pests, e.g. fungi, with other and further objects becoming apparent from a study of the within specification and accompanying examples.

It has been disclosed in Houben-Weyl, "Methoden der organischen Chemie" ("Methods of Organic Chemistry"), 4th edition, volume VIII, page 674, Georg Thieme Verlag, Stuttgart (1952), that imide-chlorides can be obtained from te corresponding carboxylic acid amides by means of thionyl chloride. However, such reactions have not yet been disclosed for compounds which contain a sulfenamide group.

The present invention provides, as new compounds, the substituted aminobenzimide-chlorides of the general formula.

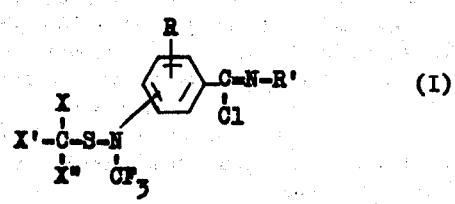

in which
X, X' and X'' each independently is fluorine, chlorine or bromine,
R is hydrogen, halogen, nitro, trifluoromethyl, or alkyl or alkoxy each with up to 3 carbon atoms, and
R' is alkyl with up to 16 carbons atoms, cycloalkyl with up to 7 carbon atoms, aralkyl with a total of up to 8 carbon atoms, or aryl with up to 10 carbon atoms.

Preferably, X, X' and X'' each independently is fluorine or chlorine; R is hydrogen, methyl, methoxy, trifluoromethyl, chlorine or nitro; and R' is alkyl with up to 12 carbon atoms, cycloalkyl with 5 or 6 carbon atoms, benzyl or phenyl.

The compounds of this invention have been found to display fungicidal properties.

The present invention also provides a process for the preparation of a compound of the formula (I), in which a substituted aminobenzamide of the general formula

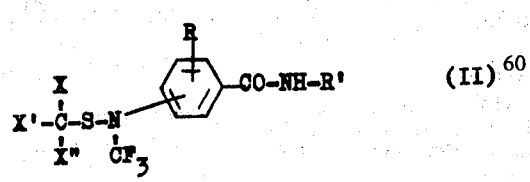

in which
X, X', X'', R and R' have the above-mentioned meanings, is reacted with a suitable chlorine-transfer agent is solution.

It is distinctly surprising that the reaction according to the present invention takes place in the manner indicated since it is known that under mild conditions sulfenamides are split with hydrogen chloride to give sulfenic acid chlorides (see Chem. Berichte 57, 755 (1924).

If 3-[N-trifluoromethyl-N-(fluorodichloromethyl-thio)-amino]-benzoic acid isopropylamide and phosphorus pentachloride are used as the starting compounds, the course of the reaction in the process according to the invention can be illustrated by the following equation:

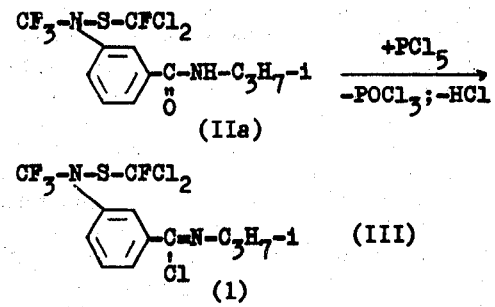

Some compounds of the formula (II) are disclosed in German specification DOS Nos. 1,543,615 and 2,064,596. The compounds that have not yet been disclosed in the literature can easily be prepared from primary amines and the corresponding aminobenzoyl fluorides as described in German patent specification No. 1,293,754 (corresponding to U.S. Pat. No. 3,547,992) the disclosure of which is incorporated herein by reference; the reaction can advantageously be carried out in benzene or toluene as the solvent, at a temperature of from 20° to 50°C.

Suitable chlorine-transfer agents which can be used in the preparative process according to the invention are phosphorus pentachloride, thionyl chloride and phosgene.

Diluents which can be used are all organic solvents which are inert to chlorine, for example methylene chloride, chloroform or chlorobenzene. Preferred inorganic solvents are excess thionyl chloride and also phosphorus trichloride and phosphorus oxychloride.

The reaction temperatures can be varied over a fairly wide range. In general, the reaction is carried out at about 0° to 150°C, preferably about 10° to 100°C.

In carrying out the process according to the invention, preferably 1 mole of phosphorus pentachloride is employed per mole of substituted aminobenzamide of the formula (II). On the other hand, if thionyl chloride is used, this chlorine-transfer agent is preferably employed in excess and, as mentioned above, can also be employed as the solvent at the same time. The working-up of the reaction mixtures can be effected by stripping off the solvent under reduced pressure and distilling the crude product, preferably under a pressure of less than 1 mm Hg.

The new substituted aminobenzimide-chlorides of the formula (I) can be used as intermediates for further organic syntheses and also as plant-protection agents, especially as fungicides.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as freon; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes (e.g. cyclohexane, etc.), paraffins (e.g.. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, et.), sulfoxides (e.g. dimethyl sulfoxide, etc.), acetonitrile, ketones (e.g. acetone, methyl ethyl ketone methyl isobutyl ketone, cyclohexanone, etc.), and/or water; as well as inert dispersible finely divided solid carriers, such as ground natural minerals (e.g. kaolins, clays, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the followiong may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other fungicides, or insecticides, acaricides, bactericides, rodenticides, nematocides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0001–10%, preferably 0.01–1%, by weight of the mixture. Thus, the present invention contemplates over-all compositions which comprise mixtures of a conventional dispersible carrier vehicle such as (1) a dispersible inert finely divided carrier solid, and/or (2) a dispersible carrier liquid such as an inert organic solvent and/or water preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1,000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

Furthermore, the present invention contemplates methods of selectively killing, combating or controlling pests, e.g. fungi, which comprises applying to at least one or correspondingly (a) such fungi, and (b) the corresponding habitat thereof, i.e. the locus to be protected, a correspondingly combative or toxic amount, i.e. a fungicidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, dry dressing, moist dressing, wet dressing, slurry dressing, encrusting, and the like.

It will be realized, of course, that the concentration of the particular active compound utilized in admixture with the carrier vehicle will depend upon the intended application. Therefore, in special cases it is possible to go above or below the aforementioned concentration ranges.

The activity of the new compounds of the present invention is illustrated, without limitation, by the following examples:

EXAMPLE 1

Mycelium growth test

Nutrient medium used:

20   parts by weight of agar-agar
    200  parts by weight of potato decoction
    5    parts by weight of malt
    15   parts by weight of dextrose
    5    parts by weight of peptone
    2    parts by weight of disodium hydrogen phosphate
    0.3  part by weight of calcium nitrate Proportion of solvent mixture to nutrient medium:

2 parts by weight of solvent mixture
100 parts by weight of agar nutrient medium
Composition of the solvent mixture:
0.19 part by weight of dimethylformamide
0.01 part by weight of alkylaryl polyglycol ether emulsifier
1.80 parts by weight of water
2 parts by weight of solvent mixture The amount of active compound required for the desired concentration of active compound in the nutrient medium was mixed with the stated amount of the solvent mixture. The concentrate was thoroughly mixed, in the stated proportions, with the liquid nutrient medium which had been cooled to 42°C, and the mixture was poured into Petri dishes of 9 cm diameter. Control plates to which the preparation had not been admixed were also set up.

When the nutrient medium had cooled and solidified, the plates were inoculated with the species of fungi stated in the table and were incubated at about 21°C.

Evaluation was carried out after 4-10 days, dependent upon the speed of growth of the fungi. When evaluation was carried out the radial growth of the mycelium on the treated nutrient medium was compared with the growth on the control nutrient medium. In the evaluation of the fungus growth, the following characteristic values were used:

1: no fungus growth
up to 3: very strong inhibition of growth
up to 5: medium inhibition of growth
up to 7: slight inhibition of growth
9: growth equal to that of untreated control.

The active compounds, the concentrations of the active compound and the results can be seen from the table which follows:

Table 1

Mycelium growth test
Fungi and bacteria
Active compounds

| Active compound | Fungi | Concentration of active compound ppm 10 |
|---|---|---|
| CF₃—N—S—CFCl₂ <br> ⟨phenyl⟩—C=N—C₃H₇—i <br> ｜ <br> Cl <br> (1) | Fusarium culmorum | 1 |
| | Sclerotinia sclerotiorum | 1 |
| | Fusarium nivale | 2 |
| | Colletotrichum coffeanum | 1 |
| | Rhizoctonia solani | 1 |
| | Pythium ultimum | 1 |
| | Cochliobolus miyabeanus | 2 |
| | Botrytis cinerea | 1 |
| | Verticillium alboatrum | 3 |
| | Piricularia oryzae | 1 |
| | Phialophora cinerescens | 1 |
| | Helminthosporium gramineum | 1 |
| | Mycosphaerella musicola | 1 |
| | Phytophthora cactorum | 1 |
| | Venturia inaequalis | 1 |
| | Pellicularia sasakii | 1 |
| | Xanthomonas oryzae | 5 |

EXAMPLE 2

Piricularia test: liquid preparation of active compound

Solvent: 1.9 parts by weight of DMF
Dispersing agent: 0.1 part by weight of alkylaryl polyglycol ether
Water: 98 parts by weight of water The amount of active compound required for the desired concentration of active compound in the spray liquor was mixed with the stated amount of the solvent and of the dispersing agent, and the concentrate was diluted with the stated amount of water.

30 rice plants about 14 days old were sprayed with the spray liquor until dripping wet. The plants remained in a greenhouse at temperatures of 22° to 24°C and a relative atmospheric humidity of about 70% until they were dry. They were then inoculated with an aqueous suspension of 100,000 to 200,000 spores/ml of Piricularia oryzae and placed in a chamber at 24°–26°C and 100% relative atmospheric humidity.

5 days after inoculation, the infection of all the leaves present at the time of inoculation was determined as a percentage of the untreated but also inoculated control plants. 0% means no infection; 100% means that the infection was exactly as great as in the case of the control plants.

The active compounds, the concentrations of the active compounds and the results can be seen from the following table:

Table 2

| Piricularia test/liquid preparation of active compound | |
|---|---|
| Active compound | Infection in % of the infection of the untreated control at an active compound concentration (by wt) of 0.025% |
| 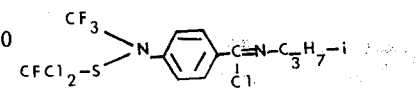 | 0 |

The synthesis of the new compounds of this invention is illustrated in and by the following preparative Examples:

EXAMPLE 3

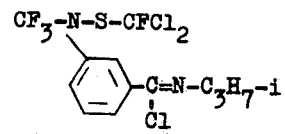

Method (a)

57 g (0.15 mole) of 3-[N-trifluoromethyl-N-(fluorodichloromethylthio)-amino]-benzoic acid isopropylamide were dissolved in 250 ml of chlorobenzene and 31.5 g (0.15 mole) of phosphorus pentachloride were added. In the course thereof, the temperature rose from 23° to 33°C and a clear solution was formed. The solution was gradually heated to 120°C, in the course of which a vigorous stream of hydrogen chloride was evolved. After completion of the evolution of gas, the phosphorus oxychloride formed and the chlorobenzene were distilled off in vacuo and the residue was distilled. This gave 58 g of 3-[N-trifluoromethyl-N-(fluorodichloromethylthio)-amino]-benzo-isopropylimide chloride of boiling point 123°–125°C/0.3 mmHg; the product had a refractive index $n_D^{20}$ of 1.5132. The yield was 96% of theory.

Method (b)

234 g of 3-[N-trifluoromethyl-N-(fluorodichloromethylthio)-amino]-benzoic acid isopropylamide were dissolved in 250 ml of thionyl chloride. On heating the solution, sulfur dioxide and hydrogen chloride were evolved continuously. After about 2 hours, an internal temperature of 85°C had been reached. After a further hour, the excess thionyl chloride was distilled off and 244 g of the above benzimidechloride, of boiling point 110°C/0.2 mmHg and refractive index $n_D^{20}$ of 1.5136, were obtained (which represented an almost quantitative yield).

The following compounds could be prepared analogously:

2-ethyl-6-[N-trifluoromethyl-N-(trifluoromethylthio)-amino]-benzo-cyclopentylimide chloride,
2-methoxy-4-[N-trifluoromethyl-N-(trichloromethylthio)-amino]-benzo-ethylimide chloride,
and the like.

It will be appreciated that the instant specification and examples are set forth by way of illustration and not limitation, and that various modifications and changes may be made without departing from the spirit and scope of the present invention.

What is claimed is:

1. A substituted aminobenzimide-chloride of the formula

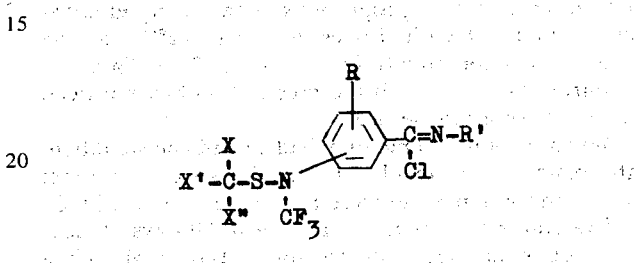

| Compound No. | Formula | Physical properties |
|---|---|---|
| 2 | CF₃\N-⟨⟩-C=N-C₃H₇-i, CFCl₂-S, Cl | Boiling point 115–118°C/0.6 mmHg, $n_D^{20} = 1.5661$ |
| 3 | CF₃-N-S-CFCl₂, ⟨⟩-C=N-⟨⟩, Cl | Boiling point 140°C/0.2 mmHg, $n_D^{20} = 1.5744$ |
| 4 | CF₃-N-S-CFCl₂, ⟨⟩-C=N-C₁₂H₂₅, Cl | $n_D^{20} = 1.5032$ |
| 5 | CF₃-N-S-CFCl₂, ⟨⟩-C=N-CH₂-⟨⟩, Cl | Boiling point 172–175°C/0.3 mmHg, $n_D^{20} = 1.5572$ |
| 6 | CF₃\N-S-CFCl₂, ⟨⟩-C=N-CH₃, Cl | Boiling point 73–76°C/0.2 mmHg, $n_D^{20} = 1.5248$ |

Other compounds which can be similarly prepared include:

2-chloro-4-[N-trifluoromethyl-N-(trifluoromethylthio)-amino]-benzo-cyclohexylimide chloride,
3-nitro-5-[N-trifluoromethyl-N-(trichloromethylthio)-amino]-benzo-p-chloro-benzylimide chloride,
2-[N-trifluoromethyl-N-(chlorodifluoromethylthio)-amino]-4-trifluoromethyl-benzonaphthylimide chloride, in which
X, X′ and X″ each independently is fluorine, chlorine or bromine,
R is hydrogen, halogen, nitro, trifluoromethyl, or alkyl or alkoxy each with up to 3 carbon atoms, and
R′ is alkyl with up to 16 carbon atoms, cycloalkyl with up to 7 carbon atoms, aralkyl with a total of up to 8 carbon atoms, or aryl with up to 10 carbon atoms.

2. A compound according to claim 1, in which X, X′ and X'' each independently is fluorine or chlorine; R is hydrogen, methyl, methoxy, trifluoromethyl, chlorine or nitro; and R' is alkyl with up to 12 carbon atoms, cycloalkyl with 5 or 6 carbon atoms, benzyl or phenyl.

3. A compound according to claim 1, wherein such compound is 3-[N-trifluoromethyl-N-(fluorodichloromethylthio)-amino]-benzo-isopropylimide chloride of the formula

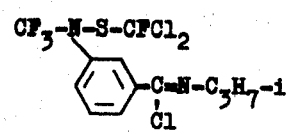

4. A compound according to claim 1, wherein such compound is 4-[N-trifluoromethyl-N-(fluorodichloromethylthio)-amino]-benzoisopropylimide chloride of the formula

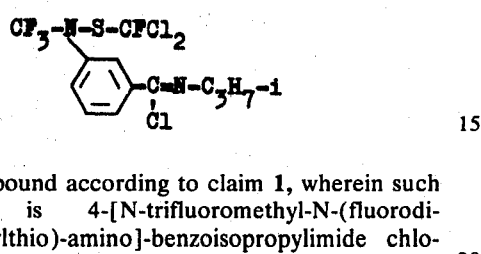

5. A compound according to claim 1, wherein such compound is 2-[N-trifluoromethyl-N-(fluorodichloromethylthio)-amino]-benzo-methylimide chloride of the formula

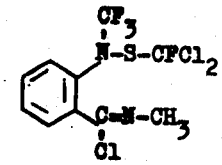

* * * * *

UNITED STATES PATENT AND TRADEMARK OFFICE
CERTIFICATE OF CORRECTION

PATENT NO. : 3,931,317
DATED : January 6, 1976
INVENTOR(S) : Engelbert Kuhle et al It is certified that error appears in the above—identified patent and that said Letters Patent are hereby corrected as shown below:

Column 1, line 21, correct spelling of "the".

Column 3, line 42, correct spelling of "following".

Column 6, Table 2, cancel structural formula and substitute therefor

-- 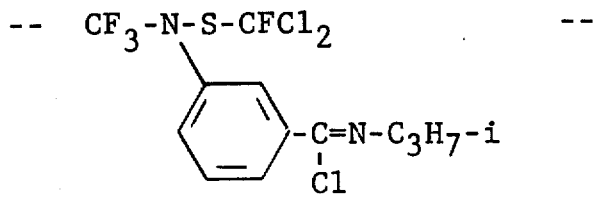 --

(1)

[SEAL]

Attest:

Signed and Sealed this twenty-ninth Day of June 1976

RUTH C. MASON
*Attesting Officer*

C. MARSHALL DANN
*Commissioner of Patents and Trademarks*